US011606978B2

United States Patent
Cornils et al.

(10) Patent No.: US 11,606,978 B2
(45) Date of Patent: Mar. 21, 2023

(54) VAPORISER INSERT FOR AN INHALER, IN PARTICULAR AN ELECTRONIC CIGARETTE PRODUCT, VAPORISER-TANK UNIT, AND AN ELECTRONIC CIGARETTE PRODUCT

(71) Applicant: KÖRBER TECHNOLOGIES GMBH, Hamburg (DE)

(72) Inventors: Lasse Cornils, Hamburg (DE); Niklas Romming, Hamburg (DE); Jan Jaklin, Freiburg (DE); Gunnar Niebuhr, Hamburg (DE); Tim Ullner, Hamburg (DE); Thomas Mueller, Hamburg (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 368 days.

(21) Appl. No.: 16/791,536

(22) Filed: Feb. 14, 2020

(65) Prior Publication Data
US 2020/0260788 A1 Aug. 20, 2020

(30) Foreign Application Priority Data
Feb. 18, 2019 (DE) .......................... 102019103990.8

(51) Int. Cl.
*A24F 40/51* (2020.01)
*A24F 40/46* (2020.01)
(Continued)

(52) U.S. Cl.
CPC .............. *A24F 40/46* (2020.01); *A24F 40/51* (2020.01); *A24F 40/57* (2020.01); *A61M 15/002* (2014.02); *A61M 15/008* (2014.02)

(58) Field of Classification Search
CPC .................................. A24F 40/51; A24F 40/57
See application file for complete search history.

(56) References Cited

U.S. PATENT DOCUMENTS

| 9,795,169 B1 | 10/2017 | Zhu | |
|---|---|---|---|
| 2015/0245659 A1* | 9/2015 | DePiano | B21D 53/06 392/397 |

(Continued)

FOREIGN PATENT DOCUMENTS

| DE | 10 2016 120 803 A1 | 5/2018 |
|---|---|---|
| EP | 2 925 395 A1 | 10/2015 |

(Continued)

OTHER PUBLICATIONS

1st Examination Report issued by the German Patent and Trademark Office dated Nov. 15, 2019 with respect to priority German Patent Application No. 10 2019 103 990.8.

(Continued)

*Primary Examiner* — Cynthia Szewczyk
(74) *Attorney, Agent, or Firm* — Saliwanchik, Lloyd & Eisenschenk (57) ABSTRACT

A vaporiser insert for an electronic cigarette product comprises at least one electrical vaporiser for vaporising fluid supplied to the vaporiser and for supplying the vaporised fluid to an airflow, a main part having a lateral face which surrounds an airflow duct through which the airflow can flow, at least one fluid opening for supplying vaporisable fluid from the outside into the vaporiser insert and to the vaporiser being arranged on the lateral face of the main part. The vaporiser insert comprises a support for retaining the vaporiser, and the support comprises a passage opening that corresponds to the fluid opening in order to supply fluid to the vaporiser.

21 Claims, 5 Drawing Sheets

(51) Int. Cl.
*A61M 15/00* (2006.01)
*A24F 40/57* (2020.01)

(56) References Cited

U.S. PATENT DOCUMENTS

| | | | |
|---|---|---|---|
| 2015/0305403 A1* | 10/2015 | Coelho Belo Fernandes De Carvalho | ............ F22B 1/284 131/328 |
| 2018/0338529 A1 | 11/2018 | Weigensberg et al. | |

FOREIGN PATENT DOCUMENTS

| | | | | |
|---|---|---|---|---|
| EP | 3 104 724 A1 | 12/2016 | | |
| WO | WO-2015066127 A1 * | 5/2015 | ............ | A24F 40/40 |
| WO | WO 2016/145611 A1 | 9/2016 | | |

OTHER PUBLICATIONS

European Search Report issued by the European Patent Office dated Jul. 17, 2020 for parallel European Patent Application No. 20157632.9.

* cited by examiner

VAPORISER INSERT FOR AN INHALER, IN PARTICULAR AN ELECTRONIC CIGARETTE PRODUCT, VAPORISER-TANK UNIT, AND AN ELECTRONIC CIGARETTE PRODUCT

CROSS REFERENCE TO RELATED APPLICATIONS

This application claims priority under 35 U.S.C. § 119(e) of German Patent Application No. DE 102019103990.8, filed on Feb. 18, 2019, which is incorporated herein by reference in its entirety.

FIELD OF INVENTION

The present invention relates to a vaporiser insert for an electronic cigarette product, comprising at least one electrical vaporiser for vaporising fluid supplied to the vaporiser and for supplying the vaporised fluid to an airflow, a main part having a lateral face which surrounds an airflow duct through which the airflow can flow, at least one fluid opening for supplying vaporisable fluid from the outside into the vaporiser insert and to the vaporiser being arranged on the lateral face of the main part. The present invention also relates to a vaporiser-tank unit and to an electronic cigarette product.

BACKGROUND OF THE INVENTION

Conventional electronic cigarette products or inhalers are based on coil and wick technology. The fluid is transported, by means of capillary forces, from a fluid reservoir, along a wick, until the fluid is heated by an electrically heated coil, and is thus vaporised. The wick functions as a fluid-conducting connection between the fluid reservoir and the heating coil that is used as the vaporiser.

A disadvantage of coil and wick technology is that an insufficient supply of fluid can lead to local overheating, as a result of which toxic substances can be released. This "dry puff", as it is known, should be avoided.

BRIEF SUMMARY OF THE INVENTION

The object of the invention is that of providing an improved vaporiser insert which in particular allows for simple and reliable assembly.

The object is achieved by the features of the independent claims.

According to the invention, the vaporiser insert comprises a support for retaining the vaporiser, in order for it to be possible to retain the vaporiser in a mechanically stable manner. Retaining the vaporiser on the support that is different or separate from the main part makes it possible for the support, together with the vaporiser, to be provided independently of the main part, in order to be combined to form the vaporiser insert according to the invention. This facilitates the assembly of the vaporiser insert and the provision of the support and of the main part as separate components.

According to the invention, the support comprises a passage opening which, for the purpose of supplying fluid to the vaporiser, corresponds to the fluid opening. The passage opening connects the fluid opening to the vaporiser in a fluid-conducting manner, in order to promote a fluid-conducting connection between the vaporiser or the vaporiser insert and an external fluid reservoir.

The passage opening is advantageously approximately the size of a base surface of the vaporiser, the surface area of an inlet side of the vaporiser, on which side fluid can enter the vaporiser, and/or the fluid opening. The passage opening is preferably provided on the inlet side of the vaporiser. This allows for the components of the vaporiser insert to be arranged as simply as possible, in particular in order for it to be possible to arrange the vaporiser on the lateral face.

The support advantageously forms an air duct for guiding the airflow, in order to promote reliable guidance and production of aerosol or vapour and to provide an integrated support by means of which factors important for the vaporisation can advantageously be determined in a manner integrated in the vaporiser insert. The support in particular forms the air duct on the outlet side of the vaporiser, through which the airflow, to which the vaporised fluid is supplied, flows or can flow. This results in reliable production of aerosol or vapour. The air enriched with vaporised fluid thus flows through the air duct, in the form of an aerosol and/or vapour.

The air duct can be understood as a support-based duct portion of the airflow duct formed by the main part. The airflow duct can open or transition into the air duct upstream of the vaporiser, at least in part, and/or the air duct can open or transition into the airflow duct downstream of the vaporiser at least in part.

The air duct is preferably formed between the support and the wall of the vaporiser insert, and/or inside the support. The contour or shape, in particular the cross section, of the support can be formed in part such that the air duct is formed between the wall of the vaporiser insert and the support, in order to promote a particularly simple structure of the support. The air duct can be formed for example inside the support, in order to promote shaping of the air duct that is particularly reliable and favourable for the aerosol quality and quantity, which shaping is independent of the shape of the wall of the main part.

The vaporiser insert according to the invention particularly advantageously makes it possible to provide a complete vaporiser which ensures reliable and reproducible vaporisation and at the same time can be easily adapted into or to an inhaler of any design.

In a preferred embodiment, the support comprises or bears electrical contacting means for electrically contacting the vaporiser insert, and/or an electrical lead in order for it to be possible to provide a multifunctional support. The electrical contacts advantageously included in the support are used for reproducible electrical contacting of an external part, for example a base part of the inhaler, in particular for supplying power to the inhaler. As a result, the external part can supply the vaporiser with electrical energy and/or control it by means of control signals. The vaporiser or the vaporiser insert can transmit signals to the external part. The electrical contacting means can for example comprise metal elements, contact springs and/or metal pins, which are borne by the support for example.

The electrical lead or the electrical leads can be used to supply power to electrical components in and/or on the support, such as the vaporiser and/or an electronic controller. The electrical lead advantageously has as low as possible an electrical resistance, in order to reduce electrical power loss. In this way, it is possible to reduce the power loss in the system to for example less than 500 mW. The shaping of the support can be adjusted such that the leads extend for example in the support and are for example moulded into or contained in the support. The electrical lead or the electrical leads can overmoulded by a plastics material that forms the support, and/or can extend on a surface of the support and thus be borne by the support.

In a preferred embodiment, the electrical contacts are arranged on an end face of the vaporiser insert, in order for it to be possible to establish a simple electrical connection to an external component, for example a component part comprising an energy store. The end faces denote the faces between which the lateral face of the main part extends.

The support is advantageously braced against a wall of the main part, in order to be able to retain the support in a particularly simple and mechanically stable manner. For this purpose, the support advantageously at least in part has a shape, in particular a cross section, that corresponds to the internal cross section of the wall of the main part. For example, the main part comprises an installation shaft which is delimited by the wall and into which the support can be inserted in order to be braced against the wall. For the purpose of retention in the main part, the support can comprise engagement parts, recesses and/or clamps, and/or can be adhesively bonded into the main part.

In a preferred embodiment, the lateral face forms the wall at least in part, in order to allow for a simple design. The support is thus arranged inside the main part. The components arranged in and/or on the support are thus encapsulated and in particular electrical components are protected from fluid.

In an advantageous embodiment, the support forms an auxiliary air duct that is different from the air duct and is intended for guiding an auxiliary airflow, in order to improve the quality of the vapour or aerosol generated. The auxiliary air duct preferably begins upstream of the vaporiser. The auxiliary airflow is advantageously supplied to the main airflow downstream of the vaporiser. For this purpose, the auxiliary air duct and the air duct can be merged downstream of the vaporiser. The auxiliary air duct can advantageously begin in the support and/or can advantageously be merged with the air duct in the support. However, embodiments are also conceivable in which the auxiliary air duct already begins upstream of the support and/or opens into the air duct downstream of the support.

The support for retaining the vaporiser advantageously comprises a ceramic substrate, in order to form the support for retaining the vaporiser in a thermally stable manner and/or to optionally thermally decouple the vaporiser from the support. The ceramic substrate is chemically and mechanically stable with respect to the temperatures of for example up to 300° C. arising during operation of the vaporiser, and to thermal load changes which arise for example approximately 200 times to 2000 times during the lifecycle of the vaporiser. Furthermore, the support is in contact with the fluid and/or the aerosol or vapour and must therefore be food-grade or biocompatible in particular at the temperatures arising during the vaporisation, and this is promoted by the ceramic substrate.

In a preferred embodiment, the support is formed of at least one or two shells, preferably made of plastics material. A single-shell or two-shell support can be conducive to a particularly simple and cost-effective embodiment. A support consisting of plastics material can be produced particularly cost-effectively, for example by means of injection moulding, and can have an advantageous geometry, in particular for air conveyance and/or for retaining the support in the main part.

A wick structure extending through the passage opening is preferably provided in order to allow for capillary fluid conduction from the external part to the vaporiser, through the fluid opening and the passage opening. This allows for a supply of fluid to the vaporiser that is independent of the orientation of the vaporiser insert and that is free of bubbles.

Advantageously, the vaporiser insert has a longitudinal axis, and an outlet side of the vaporiser is oriented so as to be in parallel with the longitudinal axis, in order to allow for effective arrangement of the vaporiser in the main part and advantageous addition of the vaporised fluid into the airflow.

The support preferably comprises a heat conduction element and/or a thermal insulation element. A thermal insulation element can be provided in order to keep the generation of heat loss and/or heat dissipation into the surroundings of the vaporiser as low as possible when the vaporiser is heated. A heat conduction element makes it possible for the waste heat of the vaporiser to be used for example to preheat the fluid when this is supplied to the vaporiser. In this way, the efficiency of the vaporisation process can be increased, since the liquid conduction is promoted by the thermally induced change in the viscosity, and less energy is required for vaporisation. The heat conduction element can be designed to use the heat generated at the vaporiser in order to bring about preheating of the supply air upstream of the vaporiser and/or reheating of the aerosol or vapour downstream of the vaporiser. The heat conduction element and/or the thermal insulation element can be used such that all materials of the vaporiser insert remain within the specified maximum temperature thereof in every operating state. The heat conduction element can advantageously consist of a metal material. The insulation element can advantageously consist of a ceramic and/or composite material.

The support preferably comprises a flow, temperature and/or filling level sensor, in order to integrate as many functions as possible into the support, and thus into the vaporiser insert. The flow sensor can measure the airflow in the air duct and/or in an auxiliary air duct. The temperature sensor can measure the temperature of the supply airflow, of the vaporiser, and/or of the generated vapour or aerosol. The filling level sensor can be designed such that the filling level of an external fluid reservoir, in which the vaporiser insert is inserted, can be measured. At least one electrical lead can be integrated in the support and/or applied to the support for one or each of the sensors. The electrical contacting means can comprise a contact, for one or each of the sensors, for reading out the relevant sensor or sensors by means of an external part.

The support preferably comprises an electronic controller in order, for example, to control the operation of the vaporiser and/or the data transfer between the support, and thus the vaporiser unit, and an external part. The electronic controller can comprise an ID chip or an identifier for identification of the vaporiser insert by an external part.

The main part is preferably cartridge-shaped or sleeve-shaped. The cartridge shape or advantageously the sleeve shape of the vaporiser insert is space-saving and advantageously has neutral shaping, which allows for the greatest possible freedom in the design of an external part surrounding the vaporiser insert, and/or an inhaler. The cartridge shape or sleeve shape of the vaporiser insert advantageously allows for versatile insertion options into different tanks. Integrating the air and/or aerosol guidance through the airflow duct inside the vaporiser insert and an advantageous connection concept via the fluid opening to different tanks provide for standardised aerosol quality and possibly improved tightness of the products, for example the inhalers.

The vaporiser insert or the main part preferably has a cross section that is constant in portions and/or tapers evenly along the flow duct in order to facilitate the assembly of the vaporiser insert. The cross section can be circular, polygonal and/or oval, in portions or entirely. A cross section that is not round, at least in portions, allows for the vaporiser insert to be installed in an external part in a non-rotatable manner.

The vaporiser insert can preferably be arranged in, in particular inserted into or pushed into, an external part, in particular in a fluid reservoir, in order to allow for simple and effective installation. The vaporiser insert is preferably an insert to be arranged, inserted, for example pushed into, driven into and/or screwed into the fluid reservoir of an inhaler.

The vaporiser insert preferably comprises at least one retaining and/or fastening element for retaining and/or fastening the vaporiser insert in the external part, in order to prevent unintentional detachment of the vaporiser insert in the external part. The vaporiser insert can also provide a counterpart to a retaining and/or fastening element in the external part. The fastening of the vaporiser insert in the external part can be detachable or non-detachable.

The vaporiser insert can preferably be mounted in the external part in a non-rotatable manner, in order to ensure that the fluid opening is for example assigned to a corresponding supply opening in the external part and/or the electrical contacting means can be brought into an operative connection with electrical contacts of a base part of the inhaler, in order for example to create a supply of electrical energy from an energy store. The vaporiser insert preferably comprises an anti-turn element on the lateral face of the main part, such as a latching element, lug, groove and/or recess.

It is advantageous for at least one air-permeable ventilation device for ventilating a fluid reservoir to be provided in the main part, in order to prevent undesired pressure differences between the fluid reservoir and the airflow duct. The vaporisation of fluid supplied from the fluid reservoir results in a negative pressure in the fluid reservoir or a pressure drop at the vaporiser, which can lead to liquid being pushed away from the vaporiser and said vaporiser thus running dry. A pressure drop at the vaporiser can also result from the device being conveyed at high altitudes, for example in the case of transportation in an aircraft, it being possible for the reduced external pressure to lead to an uncontrolled escape of liquid from the fluid reservoir. A negative pressure can also result from the consumer sucking on a mouth end of the inhaler while the vaporiser is not being heated. This can result in liquid escaping from the vaporiser. This can be prevented by means of ventilation of the fluid reservoir for example via the lateral face of the vaporiser insert, because there is then a negative pressure simultaneously at the fluid reservoir and thus at the rear face of the vaporiser or the face thereof remote from the fluid reservoir. The ventilation can be designed such that it is ensured, irrespective of the spatial orientation of the vaporiser insert, that only air can pass through the ventilation device and passage of liquid is prevented.

The vaporiser insert preferably comprises at least one retaining element, for example a bolt, on the lateral face of the main part, for the purpose of retaining a fluid supply element, in order for it to be possible for the fluid opening to be supplied with fluid irrespective of the orientation of the vaporiser insert. The fluid supply element, for example a capillary element, is designed to store fluid and supply this to a wick structure for example. As a result, even if an inhaler is briefly operated having the vaporiser insert upside down, sufficient liquid can be provided in order to allow for consumption of the inhaler.

According to the invention, a vaporiser-tank unit or a consumable unit for an electronic cigarette product comprises a vaporiser insert as described above and a fluid reservoir, the vaporiser insert being inserted into the fluid reservoir. For this purpose, the fluid reservoir can comprise an advantageous standardised fluid interface, to which the corresponding fluid opening of the vaporiser insert can be connected in a fluid-conducting and leak-free manner. The fluid interface thus resulting can comprise a seal for example. The fluid reservoir can comprise standardised retaining elements for retaining the vaporiser insert in a displacement-resistant manner. The external geometry of the fluid reservoir can thus be designed in a use-specific manner, and independently of the vaporiser insert.

The fluid reservoir preferably comprises, in a standardised manner, an insertion opening, an outlet opening, and/or an installation duct that is shaped in accordance with the external shape of the vaporiser insert and comprises an insertion opening in which the vaporiser insert can be arranged and/or pushed.

According to the invention, an electronic cigarette product comprises a vaporiser-tank unit and a base part, the vaporiser-tank unit comprising a standardised vaporiser insert and/or a vaporiser insert comprising a standardised support. The standardisation can in particular be due to the geometry and/or the electrical contacting means of the support, of the vaporiser insert and/or of the fluid reservoir.

A method for producing the vaporiser insert can comprise the following steps: providing the main part and the support, inserting and/or pushing the support into the main part, in order to provide a method for producing the vaporiser insert that is as simple and effective as possible. The support is advantageously pushed into the inside of the main part for example in order that it can bear in a stable manner against a wall of the main part.

A method for producing the vaporiser-tank unit could comprise the following steps: providing the vaporiser insert and a fluid reservoir, inserting and/or pushing the vaporiser insert into the fluid reservoir, in order to provide a method for producing the vaporiser-tank unit that is as simple and effective as possible. The vaporiser insert can in particular be inserted into an insertion opening of the fluid reservoir. In this case, the vaporiser insert, which may be longer than the fluid tank, can also protrude from the other side of the fluid reservoir in part, for example by a vapour air vent, and can optionally be shortened following insertion.

BRIEF DESCRIPTION OF THE FIGURES

The invention will be explained in the following on the basis of preferred embodiments and with reference to the accompanying drawings, in which.

DETAILED DESCRIPTION

Figure 1:
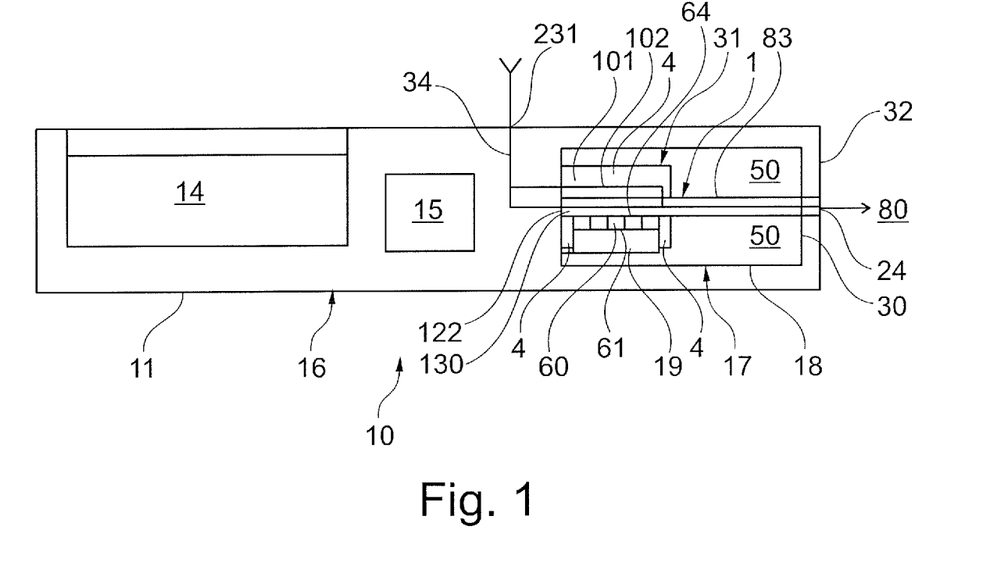
FIG. 1 is a schematic view of an electronic cigarette product.

FIG. 1 schematically shows an electronic cigarette product 10 or an inhaler. The electronic cigarette product 10 comprises a housing 11 in which an airflow duct 30 is provided between at least one air inlet opening 231 and one air outlet opening 24 at a mouth end 32 of the cigarette product 10. In this case, the mouth end 32 of the cigarette product 10 refers to the end on which the consumer drags for the purpose of inhalation, and thereby applies a negative pressure to the cigarette product 10 and generates an airflow 34 in the airflow duct 30.

The cigarette product 10 advantageously consists of a base part 16 and a consumable unit or vaporiser-tank unit 17 which comprises the vaporiser device 1 and the fluid reservoir 18 and is designed in particular in the form of a replaceable cartridge. The air sucked in through the inlet opening 231 is conducted, in the airflow duct 30, to the or through the at least one vaporiser device 1. The vaporiser device 1 is connected or can be connected to the fluid reservoir 18 in which at least one fluid 50 is stored.

The vaporiser device 1 vaporises fluid 50 that is supplied to the vaporiser device 1 from the fluid reservoir 18, advantageously by a wick or a wick structure 19 by means of capillary forces, and adds the vaporised fluid into the airflow 34, as aerosol/vapour, at an outlet side 64.

The porous and/or capillary, fluid-conducting wick structure 19 is advantageously arranged on an inlet side 61 of the heater 60, as shown schematically in FIG. 1. One fluid interface and/or a plurality of fluid lines may be provided between the fluid reservoir 18 and wick structure 19. The fluid reservoir 18 can therefore also be arranged so as to be spaced apart from the wick structure 19. The wick structure 19 advantageously contacts the inlet side 61 of the heater 60 over the entire surface, and covers all fluid ducts 62 of the heater 60 on the inlet side. On the side opposite the heater 60, the wick structure is connected to the fluid reservoir 18 in a fluid-conducting manner. The dimensions of the fluid reservoir 18 may be greater than those of the wick structure 19. The wick structure 19 can for example be inserted into an opening in a housing of the fluid reservoir 18. It is also possible for a plurality of vaporiser devices 1 to be associated with one fluid reservoir 18. The wick structure 19 can in general be integral or formed in multiple parts.

The wick structure 19 consists of porous and/or capillary material which, owing to capillary forces, is capable of passively supplying a sufficient amount of fluid, vaporised by the heater 60, from the fluid reservoir 18 to the heater 60, in order to prevent the fluid ducts 62 running dry and the problems resulting therefrom.

The wick structure 19 advantageously consists of an electrically non-conductive material, in order to prevent undesired heating of fluid in the wick structure 19 by means of a flow of current. The wick structure 19 advantageously has low thermal conductivity. The wick structure 19 advantageously consists of one or more of the materials including cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable conveying rate, or a compound of two or more of the above-mentioned materials. In an advantageous practical embodiment, the wick structure 19 can comprise at least one ceramic fibre paper and/or a porous ceramic. The volume of the wick structure 19 is preferably in the range between 1 mm^3 and 10 mm^3, more preferably in the range between 2 mm^3 and 8 mm^3, even more preferably in the range between 3 mm^3 and 7 mm^3, and is for example 5 mm^3.

If the wick structure 19 consists of an electrically and/or thermally conductive material, an insulation layer consisting of an electrically and/or thermally insulating material, for example glass, ceramic or plastics material, comprising openings that extend through the insulation layer and correspond to the fluid ducts 62, is advantageously provided between the wick structure 19 and the heater 60.

An advantageous volume of the fluid reservoir 18 is in the range between 0.1 ml and 5 ml, preferably between 0.5 ml and 3 ml, more preferably between 0.7 ml and 2 ml, or 1.5 ml.

Figure 6:
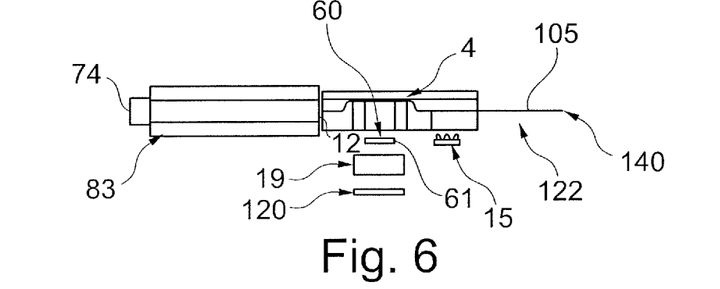
FIGS. 6 and 7 each show the production of a vaporiser insert.
Figure 7:
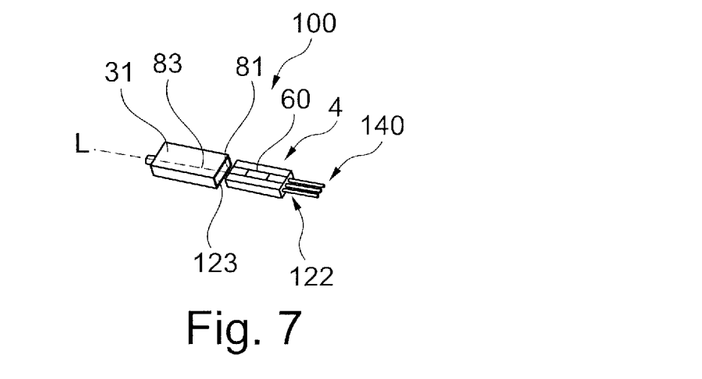

The electronic cigarette 10 further comprises an electrical energy store 14 and an electronic controller 15. The energy store 14 is generally arranged in the base part 16 and can in particular be an electrochemical primary cell or a rechargeable electrochemical battery, for example a lithium ion battery. The vaporiser-tank unit 17 is arranged between the energy store 14 and the mouth end 32. The electronic controller 15 comprises at least one digital data processing device, in particular a microprocessor and/or microcontroller, in the base part 16 (as shown in FIG. 1) and/or in the vaporiser-tank unit 17 or a vaporiser insert 100 (as shown in FIGS. 6 and 7).

A sensor, for example a pressure sensor or a pressure or current switch, is advantageously arranged in the housing 11, the controller 15 being able to determine, on the basis of a sensor signal emitted by the sensor, that a consumer is dragging on the mouth end 32 of the cigarette product 10 in order to inhale. In this case, the controller 15 actuates the vaporiser device 1 in order to add fluid 50 from the fluid reservoir 18 into the airflow 34 in the form of aerosol/vapour.

The vaporiser device 1 or the at least one vaporiser 60 is arranged in a part of the vaporiser-tank unit 17 remote from the mouth end 32. As a result, effective electrical coupling and actuation of the vaporiser device 1 is possible. The airflow 34 advantageously leads to the air outlet opening 24 via an airflow duct 30 extending axially through the fluid reservoir 18.

The fluid 50 that is stored in the fluid reservoir 18 and is to be metered is for example a mixture of 1,2-propylene glycol, glycerine, water, at least one aroma (flavour), and/or at least one active ingredient, in particular nicotine. However, the specified components of the fluid 50 are not essential. In particular, aromatic and/or active ingredients, in particular nicotine, can be omitted.

The vaporiser-tank unit or cartridge 17, or the base part 16, advantageously comprises a non-volatile data memory for storing information or parameters relating to the vaporiser-tank unit or cartridge 17. The data memory can be part of the electronic controller 15. Information on the composition of the fluid stored in the fluid reservoir 18, information on the process profile, in particular power and/or temperature control, data relating to state monitoring or a system check, for example a tightness check, data relating to copy protection and protection against counterfeiting, an ID for clearly identifying the vaporiser-tank unit or cartridge 17, a serial number, production date and/or expiry date, and/or puff count (number of inhalations by the consumer) or the usage time is/are advantageously stored in the data memory. Advantageously, the data memory is or can be electrically connected to the controller 15.

It is also possible for user-related data, in particular relating to smoking behaviour, to be stored, and preferably also used for controlling the inhaler, in the inhaler 10 and/or in an external memory which can be connected for communication to the inhaler 10, at least at times, in a suitable manner that is known per se.

A main part 83 and a support 4 form a vaporiser insert 100 (see FIG. 2) which is fluid-tight and does not allow any fluid 50 to penetrate into the interior of the vaporiser insert 100, in order to prevent undesired escape of fluid 50 from the airflow duct 30 and/or the vaporiser-tank unit 17. The seal of the vaporiser insert 100 is designed such that fluid 50 can only pass through the wick structure 19 and subsequently through the vaporiser 60, and is added to the airflow 34 in the vaporised state. In order to achieve fluid-tightness, it is possible for adhesive bonds, interference fits, additional sealing materials such as a seal 120, and/or welded connections to be used after or during installation of the vaporiser-tank unit 17. For the purpose of ventilation of the fluid reservoir 18, the vaporiser insert 100 can comprise a semi-permeable membrane which allows air to enter the fluid reservoir 18 and does not allow any fluid 50 to escape from the fluid reservoir 18.

Figure 2:
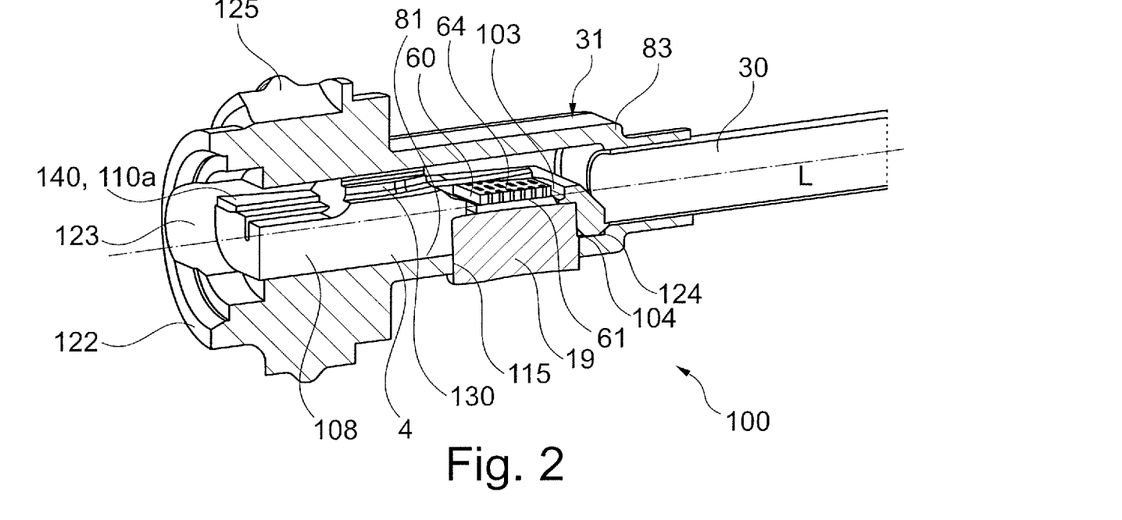
FIG. 2 is a cross section through a vaporiser insert.

The vaporiser insert 100 comprises the main part 83 having a lateral face 31 arranged around the airflow duct 30 (see FIG. 2). The airflow duct 30 extends through the vaporiser insert 100. The airflow duct 30 extends substantially along a longitudinal axis L, the main part 83 having the greatest extension along the longitudinal axis L.

The vaporiser insert 100 comprises a support 4 that is explained with reference to FIG. 3. The support 4 bears against a wall 81 of the main part 83, the lateral face 31 forming the wall 81 on which the main plate 121 and a bulge 109 of the support 4 bear. For this purpose, the support 4 at least in part has a cross section that corresponds to the cross section of the wall 81.

The bulge 109 has a cross section that is round at least in part and that corresponds to the internal cross section of a wall 81 of the main part 83. The dimensions of the substantially plate-shaped main plate 121 have an edge length which is equal to the internal cross section of the main part 83, in order that it can be reliably retained in the main part 83.

Inside the bulge, the support 4 forms an air duct 130 for guiding the airflow 34. The bulge 109 can furthermore make it possible to retain the support 4 or the shell 108 in the main part 83 of the vaporiser insert 100 (see FIGS. 2 and 5).

The vaporiser insert 100 comprises the vaporiser 60 that is retained by the support 4. The outlet side 64 faces the inside of the vaporiser insert 100 or the air duct 130. The vaporiser 60 is arranged such that the advantageously planar outlet side 64 is arranged so as to be in parallel with the longitudinal axis L, in order that the airflow 34 can advantageously flow thereover. In other embodiments, the outlet side 64 can also be curved and/or arranged so as to be inclined relative to the longitudinal axis, in order to adjust the overflow to the outlet side 64.

The air duct 130 transitions into the airflow duct 30 downstream of the vaporiser 60. The air duct 130 can be understood to be the flow portion of the airflow duct 130 that is formed by the support 4.

The structure of the support 4, in particular the arrangement of the air duct 130 and the outlet side 64 of the vaporiser 60, ensure a flow speed, in the aerosol phase, that prevents droplets in the airflow 34 from being collected on the walls 31 of the main part 83, on the support 4, and/or on airflow deflection points, by means of collision, and fluid 50 thus escaping from the inhaler 10. The air pressure at the vaporiser 60, in particular a negative pressure, the dragging resistance, and/or turbulence in the airflow 34 can be controlled by the cross section of the airflow duct 30 and/or purposeful constrictions. This can influence the airflow 34 when it encounters the vaporiser 60 and the aerosol quality, for example the mixing and/or droplet size.

Additional ducts, in particular at least one auxiliary air duct 101 that guides an auxiliary airflow 102, which meet the air duct 130 downstream of the vaporiser 60, can ensure mixing of the gas/aerosol mixture with inlet air and/or can control processes of subsequent treatment and/or of recondensation (see FIG. 1). An optionally adjustable cross section of the airflow duct 30 and/or of an auxiliary air duct 101 allows the user to set an individual dragging resistance and/or an individual aerosol quality.

The support 4 or the shell 108 comprises a passage opening 104 (see FIGS. 2 and 3). A ceramic substrate 103 for retaining a vaporiser 60 is arranged around the passage opening 104. The ceramic substrate 103 can consist of a low temperature co-fired ceramic (LTCC). The ceramic substrate 103 can be used for thermally decoupling the vaporiser 60 and the main plate 103, and is heat-resistant and thermally stable.

The inlet side 61 of the vaporiser 60 is advantageously connected to a wick structure 19 in a fluid-conducting manner. The wick structure 19 is explained with reference to FIGS. 1 and 8 and advantageously extends through the passage opening 104. The passage opening 104 is advantageously dimensioned such that the wick structure 19 can extend through the passage opening 104. The wick structure 19 can also be supported and retained in the passage opening 104. Alternatively, the vaporiser 60 can extend through the passage opening 104 in order to be contacted by the wick structure 19 in a fluid-conducting manner on the inlet side. In this embodiment, the wick structure 19 can for example have a larger cross section than the passage opening 104.

A fluid opening 115 for supplying vaporisable fluid 50 from the outside into the vaporiser insert 100 and to the vaporiser 60 is arranged on the lateral face 31 of the main part 83 (see FIG. 2). The passage opening 104 that corresponds to the fluid opening 115, in order to supply fluid to the vaporiser 60, and the fluid opening 115 can connect an external part, for example a fluid reservoir 18, to the vaporiser 60 in a fluid-conducting manner. The passage opening 104 is arranged on the support 4 such that the size and/or position thereof, in the installed state, allows for transport of fluid 50 through the fluid opening 115. For example, the fluid opening 115 and the passage opening 104 can be of similar or the same dimensions. In this embodiment, the passage opening 104 is the same size as the fluid opening 115. In the installed state of the vaporiser insert 100, the passage opening 104 is arranged so as to overlap with the fluid opening 115 at least in part.

The wick structure 19 can extend through the fluid opening 115 and/or the passage opening 104. The wick structure 19 can both be connected to the inlet side 61 of the vaporiser 60 in a fluid-conducting manner and can also be arranged in an external part 18 for the purpose of receiving fluid 50. For this purpose, the wick structure 19 can end flush with the lateral face 31 or protrude beyond the lateral face 31. The wick structure 19 can be retained by the passage opening 104 and/or the fluid opening 115.

The main part 83 advantageously comprises an installation shaft 123 for inserting or pushing in the support 4. The installation shaft 123 is advantageously delimited by the wall 81. The support 4 can be pushed into the installation shaft 123 as far as the point at which the installation shaft 123 ends, for example at a constriction 124 or a stop. The length of the installation shaft 123 is advantageously at least equal to the length of the support 4, such that the support 4 can end flush with the end 122 located upstream of the vaporiser 60, and/or is displaced into the main part 83, along the longitudinal axis L, relative to the end 122.

For advantageous handling of the vaporiser insert 100, the main part 83 comprises a collar 125 and/or a baseplate 7 (see FIG. 9) at the end 122 located upstream of the vaporiser 60, which collar and/or baseplate extends axially from the lateral face 31 of the main part 83.

Figure 3:
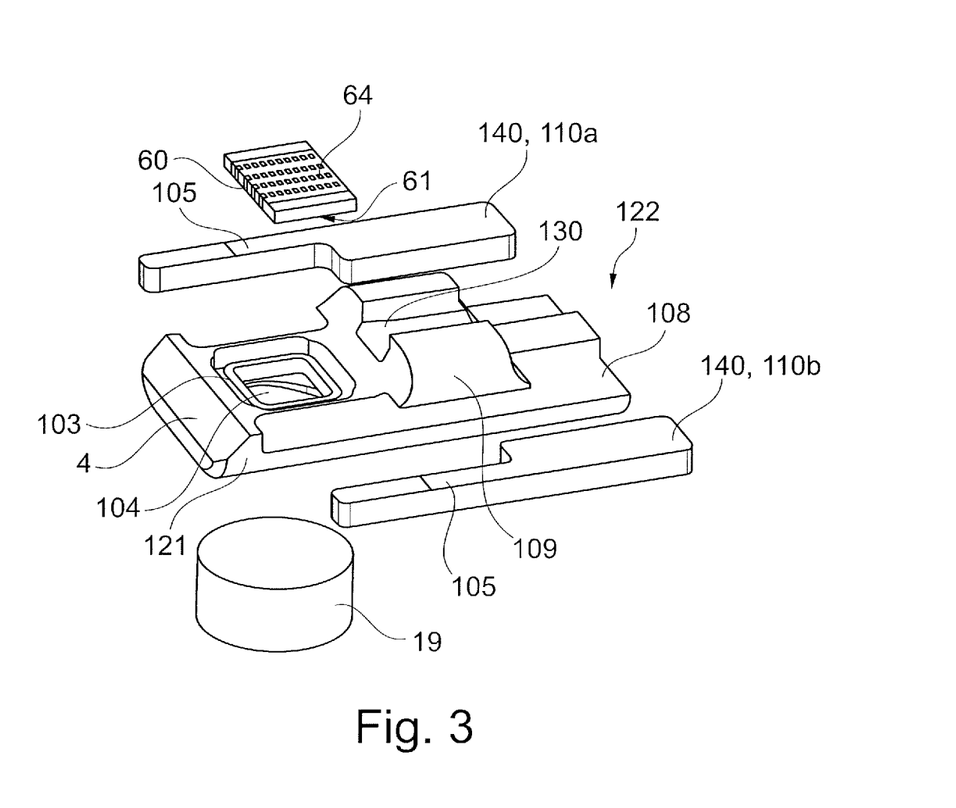
FIG. 3 is an exploded view of a support.

The support 4 for the vaporiser insert 100 comprises a shell 108 comprising a substantially plate-shaped base surface 121 (see FIG. 3). The shell 108 is manufactured from a plastics material for example, in particular a high-temperature plastics material such as PEEK, which is chemically and mechanically stable at the temperatures of up to 300° C. that arise during vaporisation.

The shaping or geometry of the support 4 is advantageously adjusted such that the necessary air guidance is integrated. Corresponding recesses and/or shapings, for example the bulge 109, can direct the supply air to the vaporiser 60, the overflow of the vaporiser 60, and/or the guidance of the aerosol or vapour. The vaporisation can thus be optimised by the airflow 34 being adjusted, at the outlet side 64 of the vaporiser 60, such that a desired quantity of droplets of a corresponding size is added to the airflow 34.

The support 4 or the shell 108 comprises electrical contacting means 140 for the electrical power supply of the vaporiser insert 100 and/or for receiving control signals for the vaporiser 60. In this case, the electrical contacting means 140 comprises two electrical contacts 110a, 110b. In order to supply the vaporiser 60 with electrical energy, the electrical contacts 110a, 110b are connected to the vaporiser 60, via electrical leads 105, from an end 122 of the support 4 that is advantageously located upstream of the vaporiser 60. The end 122 located upstream of the vaporiser 60 is the end that is designed, by way of the electrical contacting means 140, for mechanical and/or electrical connection to an external part, for example a base part 16 of the inhaler 10. The electrical leads 105 preferably extend in parallel with the air duct 130.

In this example, the electrical contacting means 140 comprises precisely two electrical contacts 110a, 110b in order to be able to provide a very simple electrical and thus also mechanical interface between the vaporiser insert 100 and an external part. In this case, signals can be separated for example by means of filters, multiplexers and/or demultiplexers such that sensor data can be read out or signals can be transmitted to sensors between heat pulses.

The support 4 is designed as a standardised component. As many functions as possible of the vaporiser insert 100, for example the electrical control and/or the air guidance, are integrated in the support 4 or in components contained in the support 4. As many functions as possible are integrated in the vaporiser insert 100 in a standardised manner, in particular the vaporiser 60, the wick structure 19, the electrical contacting means 140, electrical leads 105, an electronic controller 15 for example comprising an ID, and defined air guidance which is formed for example by the air duct 130 in the region of the vaporiser 60.

Figure 4:
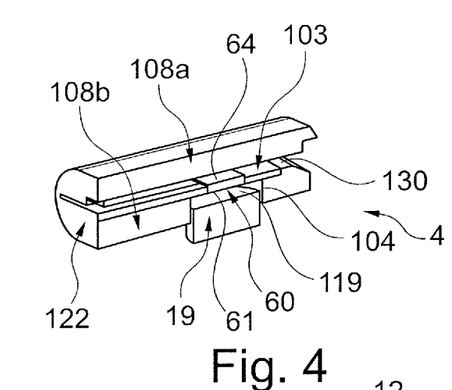
FIG. 4 is a cross section through a support.

FIG. 4 is a cross section through a support 4 for a vaporiser insert 100. The support 4 is formed of two shells 108a, 108b. The shells 108a, 108b are arranged such that the air duct 130 is formed between the shells 108a, 108b. The air duct 130 is thus arranged in the interior of the support 4. The shells 108a, 108b can be arranged as a lower shell 108b and an upper shell 108a.

One of the shells 108a, 108b for example comprises the passage opening 104 for arranging the wick structure 19. A non-woven fabric 119 can be arranged between the inlet side 61 and the wick structure 19 for the purpose of improved fluid transport. For example, the non-woven fabric 119 can be particularly thermally and/or chemically stable, and/or can have a different fluid conduction and/or fluid storage capacity from the wick structure 19.

One of the shells 108a, 108b advantageously comprises a ceramic substrate 103 for retaining the vaporiser 60. The ceramic substrate 103 is advantageously retained by the shell 108b, which also comprises the passage opening 104.

The external cross section of the support 4 or portions of the shells 108a, 108b that face outwards in the installed state are curved, for example round and/or semi-circular, at least in part. The shape of the support 4 or the shells 108a, 108b is advantageously designed such that the support 4 can be arranged, supported and retained inside the main part 83, as shown in FIG. 5.

Figure 5:
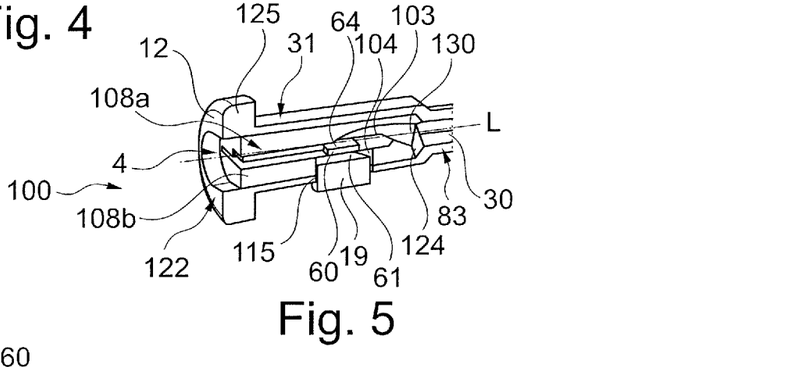
FIG. 5 is a cross section through a vaporiser insert.

FIG. 5 is a cross section through a vaporiser insert 100 according to the invention, comprising the support 4, having two shells 108a, 108b, that is explained with reference to FIG. 4.

The support 4 can be inserted into the installation shaft 123 as a fully assembled unit, comprising the shells 108a, 108b. It is also possible, however, for first one shell 108a and then the other shell 108b to be inserted into the installation shaft 123. The shells 108a, 108b can for example be clamped, adhesively bonded, welded and/or soldered together.

FIGS. 6 and 7 each show the production of a vaporiser insert 100 as shown in FIG. 2, FIG. 6 being a longitudinal sectional view of the vaporiser insert 100 and FIG. 7 being a perspective view of the vaporiser insert 100. FIGS. 6 and 7 each show the support 4, the main part 83 and the vaporiser 60.

In FIG. 6, the vaporiser 60 is arranged in the support 4. A wick structure 19 is advantageously arranged on the inlet side 61 of the vaporiser 60. The vaporiser 60 and/or the wick structure 19 can preferably be sealed, by means of a seal 120, in order to improve the fluid-tightness with respect to the support 4.

The support 4 can comprise an electronic controller 15 or a part of an electronic controller 15, for example an electronically identifiable identification. The identifiable identification can preferably comprise an ID chip, for example an SMD EEPROM. The electrical leads 105 required therefor are advantageously integrated in the support 4 at least in part, as shown in FIGS. 6 and 7. The electrical leads 105 are also used for electrical power supply and control of the vaporiser 60.

The support 4 comprises the electrical contacting means 140 for electrically connecting the support 4 and thus the vaporiser insert 100 to an external part, in particular a base part 16 of an inhaler 10.

In FIG. 6, the support 4 is provided for being installed in the main part 83.

As shown in FIG. 7, the provided support 4 can be inserted into the main part 83. For example, the support 4 can be inserted or pushed into the main part 83, in particular into the installation shaft 123, along the longitudinal axis L.

In this embodiment, the electrical contacting means 140 comprises three electrical contacts which, in the installed state, extend out of the main part 83 in the longitudinal direction. This can be conducive to electrical contacting between the vaporiser insert 100 and an external part. Three electrical contacts 110a, 110b, 110c can be provided for example, in order to provide earthing, a control signal and/or a data transmission signal (see also FIG. 9).

However, in other embodiments, the electrical contacting means 140 or the main part 83 can be designed such that, in the installed state, the electrical contacting means 140 are arranged in the installation shaft 123, in order to be mechanically protected.

The support 4 retains the components of the vaporiser insert 100 in a manner so as to be mechanically stable with respect to one another and connects said components as shown in FIGS. 2 to 7. The individual components in particular comprise the vaporiser 60, the wick structure 19 comprising advantageously flexible wick components, and/or the non-woven fabric 119, advantageously electrical leads 105, electrical contacting means 140, advantageously the electronic controller 15 and the air duct 130. In this case, clamped connections, adhesive connections, welded connections, soldered connections, sintered connections and/or other mechanical connection variants can be used. The mechanical connections between the components are designed such that the connections remain stable even at the operating temperature of the vaporiser 60 and/or withstand the pressures resulting from the generation of gas during liquid vaporisation.

Figure 8:
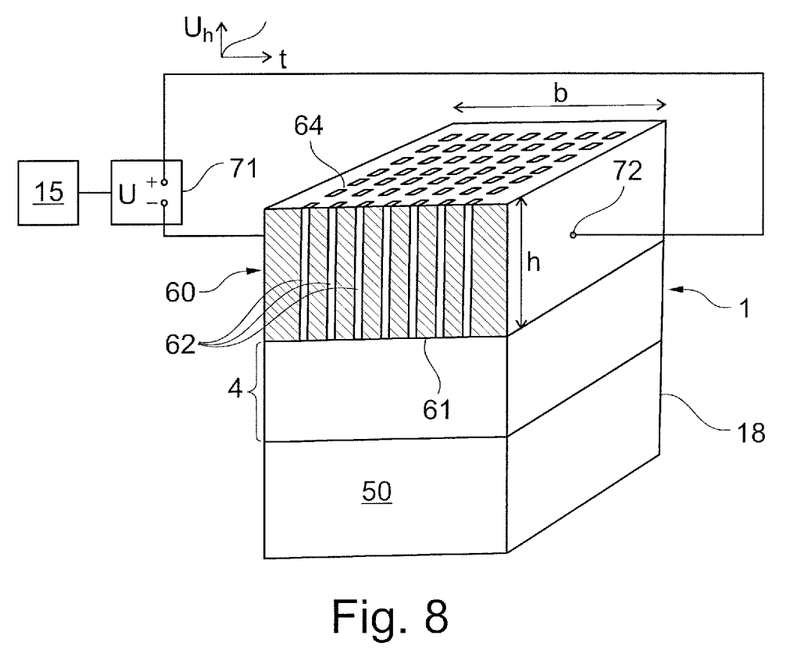
FIG. 8 is a perspective view of a vaporiser comprising a fluid reservoir.

A vaporiser device 1 according to FIG. 8 comprises a block-like, preferably monolithic, heater 60, preferably consisting of an electrically conductive material, in particular a doped semiconductor material, preferably silicon, and a support 4 comprising a passage opening 104 for the purpose of connecting the heater 60 and a fluid reservoir 18 in a fluid-tight manner, advantageously by means of a wick structure 19 that is arranged in the passage opening 104. It is not necessary for the entire heater 60 to consist of an electrically conductive material. It may be sufficient, for example, for the surface of the heater 60 to be provided with an electrically conductive, for example metal, coating, or preferably to be suitably doped. In this case, it is not necessary for the entire surface to be coated; for example, metal or preferably non-metal conductors or metal conductors laminated in a non-metal can be provided on a non-conductive or semi-conductive base body. It is also not essential for the entire heater 60 to produce heat. It may be sufficient, for example, for heat to be produced by a portion or a heating layer of the heater 60 in the region of the outlet side 64.

The heater 60 is provided with a plurality of microchannels or fluid ducts 62 which connect an inlet side 61 of the heater 60 to an outlet side 64 of the heater 60 in a fluid-conducting manner. The inlet side 61 is connected to the fluid reservoir 18 in a fluid-conducting manner by means of a wick structure 19 (not shown in FIG. 8). The wick structure 19 is used for passively conveying fluid from the fluid reservoir 18 to the heater 60 by means of capillary forces.

The average diameter of the fluid ducts 62 is preferably in the range between 5 µm and 200 µm, more preferably in the range between 30 µm and 150 µm, even more preferably in the range between 50 µm and 100 µm. By virtue of these dimensions, a capillary effect is advantageously achieved, such that fluid entering a fluid duct 62, on the inlet side 61, rises upwards through the fluid duct 62 until the fluid duct 62 is filled with fluid. The volume ratio of fluid ducts 62 to heater 60, which can be referred to as the porosity of the heater 60, is for example in the range between 10% and 50%, advantageously in the range between 15% and 40%, more advantageously in the range between 20% and 30%, and is for example 25%.

The edge lengths of the surfaces of the heater 60 provided with fluid ducts 62 are for example in the range between 0.5 mm and 3 mm, preferably between 0.5 mm and 1 mm. The dimensions of the surfaces of the heater 60 provided with fluid ducts 62 can for example be: 0.95 mm×1.75 mm or 1.9 mm×1.75 mm or 1.9 mm×0.75 mm. The edge lengths of the heater 60 can for example be in the range between 0.5 mm and 5 mm, preferably in the range between 0.75 mm and 4 mm, more preferably in the range between 1 mm and 3 mm. The surface of the heater 60 (chip size) can be for example 1 mm×3 mm, 2 mm×2 mm or 2 mm×3 mm.

The width b of the heater 60 (see FIG. 8) is preferably in the range between 1 mm and 5 mm, more preferably in the range between 2 mm and 4 mm, and is for example 3 mm. The height h of the heater 60 (see FIG. 8) is preferably in the range between 0.05 mm and 1 mm, more preferably in the range between 0.1 mm and 0.75 mm, even more preferably in the range between 0.2 mm and 0.5 mm, and is for example 0.3 mm. Even smaller heaters 60 can be manufactured, provided and operated in a functional manner.

The number of fluid ducts 62 is preferably in the range between four and 1000. In this way, the heat input into the fluid ducts 62 can be optimised, and a guaranteed high vaporisation efficiency and a sufficiently large vapour discharge surface can be achieved.

The fluid ducts 62 are arranged in the form of a square, rectangular, polygonal, round, oval or differently shaped array. The array can be formed in the manner of a matrix having s columns and z rows, s advantageously being in the range between 2 and 50, and more advantageously in the range between 3 and 30, and/or z advantageously being in the range between 2 and 50, and more advantageously in the range between 3 and 30. In this way, an effective and easily producible arrangement of the fluid ducts 62 having a guaranteed high vaporisation efficiency can be achieved.

The cross section of the fluid ducts 62 can be square, rectangular, polygonal, round, oval or differently shaped, and/or can change in regions, in particular become larger or smaller or remain constant, in the longitudinal direction.

The length of one or each fluid duct 62 is preferably in the range between 100 µm and 1000 µm, more preferably in the range between 150 µm and 750 µm, even more preferably in the range between 180 µm and 500 µm, and is for example 300 µm. In this way, it is possible to achieve optimum fluid uptake and portioning with sufficiently good heat input from the heater 60 into the fluid ducts 62.

The spacing between two fluid ducts 62 is preferably at least 1.3 times the internal diameter of one fluid duct 62, the spacing being based on the central axes of the two fluid ducts 62. The spacing can preferably be 1.5 to 5 times, more preferably 2 to 4 times, the inside diameter of one fluid duct 62. It is thus possible to achieve optimum heat input into the heater 60 and a sufficiently stable arrangement and wall thickness of the fluid ducts 62.

Owing to the described features, the heater 60 can also be referred to as a volume heater, in particular if the heater 60 is designed such that substantially the entire volume is electrically conductive, and is designed as a resistance heater.

The vaporiser device 1 comprises a heater voltage source 71 that can preferably be controlled by the controller 15 and that is connected to the heater 60 by means of electrodes 72 on opposing sides of said heater, such that an electrical voltage Uh generated by the heater voltage source 71 results in a current flow through the heater 60. Owing to the ohmic resistance of the electrically conductive heater 60, the current flow results in heating of the heater 60 and thus in vaporisation of fluid contained in the fluid ducts 62. Vapour/aerosol 6 generated in this manner escapes from the fluid ducts 62 to the outlet side 64 and is mixed into the airflow 34 (see FIG. 1). The controller 15 actuates the heater voltage source 71 more precisely when an airflow 34 through the airflow duct 30, caused by the consumer dragging, is identified, spontaneous heating causing the fluid located in the fluid ducts 62 to be driven out of the fluid ducts 62 in the form of vapour/aerosol.

In this case, the duration of the individual vaporisation steps at different temperatures and/or vaporisation of the individual components of the individual portions of the fluid can be kept sufficiently short and/or can take place in a manner clocked at a control frequency such that the stepwise vaporisation is not noticed by a consumer and it is nonetheless possible to ensure aerosol formation that is largely homogeneous, has a consistent taste, and is reproducibly precise.

An electronic or electrical connection of the heater 60 can be achieved for example by means of clamped, spring or press-in contacts, wirebonding and/or soldering.

A voltage curve Uh(t) that is adjusted to the fluid mixture used is preferably stored in the data memory of the inhaler 10. This makes it possible to specify the voltage curve Uh(t) in a manner adjusted to the liquid used, such that the heating temperature of the heater 60, and thus also the temperature of the capillary fluid ducts 62, can be controlled temporally over the vaporisation process, in accordance with the known vaporisation kinetics of the relevant liquid, as a result of which optimum vaporisation results can be achieved. The vaporisation temperature is preferably in the range between 100° C. and 400° C., more preferably between 150° C. and 350° C., even more preferably between 190° C. and 290° C.

The heater 60 can advantageously be produced from segments of a wafer, by means of thin-film technology, preferably having a layer thickness of less than or equal to 1000 μm, more preferably 750 μm, even more preferably less than or equal to 500 μm. Surfaces of the heater 60 can advantageously be hydrophilic. The outlet side 64 of the heater 60 can advantageously be microstructured or comprise micro recesses (micro grooves).

The vaporiser device 1 is adjusted such that a quantity of fluid preferably in the range between 1 μl and 20 μl, more preferably between 2 μl and 10 μl, even more preferably between 3 μl and 5 μl, typically 4 μl per drag by the consumer, is metered in. The vaporiser device 1 can preferably be adjustable with respect to the quantity of fluid/vapour per drag, i.e. per drag duration from 1 s to 3 s.

In the following, the course of the vaporisation process will be explained by way of example.

In an initial state, the voltage source 71 or the energy store 14 for the heating process is disabled.

In order to vaporise fluid 50, the voltage source 14, 71 for the heater 60 is activated. In this case, the voltage Uh is set such that the vaporisation temperature in the heater 60, and thus in the fluid ducts 62, is adjusted to the individual vaporisation behaviour of the fluid mixture used. This prevents the risk of local overheating and thus the formation of toxic substances.

In particular, it is also possible to counteract or counter or prevent undesired differential vaporisation of a liquid mixture. A liquid mixture could otherwise lose components prematurely, during the course of vaporisation processes, in particular “puffs”, owing to different boiling temperatures, before the reservoir 18 of liquid 50 is entirely emptied, which could result in undesired effects for the user during operation, such as inconsistent metering, in particular in the case of a pharmaceutically effective liquid.

As soon as a quantity of fluid is vaporised that corresponds or is in relation to the volume of the fluid ducts 62, the heater voltage source 71 is deactivated. Since the liquid properties and quantity are advantageously known exactly and the heater 60 has a measurable temperature-dependent resistance, this timepoint can be determined or controlled very precisely. The energy uptake of the vaporiser device 1 can therefore be reduced compared with known devices, since the necessary vaporisation energy can be introduced in a more metered, and thus more exact, manner.

After completion of the heating process, the fluid ducts 62 are largely or completely emptied. The heater voltage 71 is then disabled until the fluid ducts 62 are filled again, by means of re-supplying fluid through the wick structure 19. As soon as this is the case, the next heating cycle can be started by enabling the heater voltage 71.

The actuation frequency of the heater 60, generated by the heater voltage source 71, is generally advantageously in the range of from 1 Hz to 50 kHz, preferably in the range of from 30 Hz to 30 kHz, more preferably in the range of from 100 Hz to 25 kHz.

The frequency and the duty factor of the heater voltage Uh for the heater 60 are advantageously adjusted to the natural oscillation or natural frequency of the bubble oscillations during bulk boiling. The period 1/f of the heater voltage can therefore advantageously be in the range between 5 ms and 50 ms, more advantageously between 10 ms and 40 ms, even more advantageously between 15 ms and 30 ms, and can for example be 20 ms. Depending on the composition of the vaporised fluid 50, frequencies other than those mentioned can be optimally adjusted to the natural oscillation or natural frequency of the bubble oscillations.

It has furthermore been found that the maximum heater current generated by the heater voltage Uh should preferably be not more than 7 A, more preferably no more than 6.5 A, even more preferably no more than 6 A, and optimally in the range between 4 A and 6 A, in order to ensure concentrated vapour while preventing overheating.

The conveying rate of the wick structure 19 is in turn optimally adjusted to the vaporisation rate of the heater 60, such that sufficient fluid 50 can be supplied at all times, and the region in front of the heater 60 is prevented from running dry.

The vaporiser device 1 is preferably produced on the basis of MEMS technology, in particular from silicon, and is therefore advantageously a micro-electro-mechanical system.

In accordance with what has been said above, a layer structure consisting of an Si-based heater 60 that is advantageously planar at least on the inlet side 61 and of one or more capillary structures 19 that are located therebelow and advantageously have different pore sizes is advantageously proposed. The wick structure 19 that is arranged directly on the inlet side 61 of the heater 60 prevents the formation of bubbles on the inlet side 61 of the heater 60, since gas bubbles prevent a further conveying effect and at the same time lead to (local) overheating of the heater 60 owing to a lack of cooling by liquid subsequently flowing through.

FIG. 9 is a longitudinal section through a vaporiser-tank unit 17. The vaporiser insert 100 is a schematic view of the vaporiser insert 100 as described in FIGS. 2 and 5, the support 4 of the vaporiser insert 100 being single-shelled.

The vaporiser insert 100 comprises opposingly arranged end faces 11, 12 and the main part 83 between the end faces 11, 12, which main part is arranged around the airflow duct 30 through which the airflow 34 can flow. The longitudinal axis L is defined along the airflow duct 30 and/or between the end faces 11, 12. The main part 83 extends along the longitudinal axis L or the airflow duct 30 between the end faces 11, 12.

The vaporiser insert 100 is cartridge-shaped or sleeve-shaped. In this example, the main part 83 has a cross section that is round in portions. The longitudinal extension along the airflow duct 30 is greater than the diameter of the main part 83. As a result, the vaporiser insert 100 is elongate. The vaporiser insert 100 is preferably of a length of from 0.1 cm to 10 cm, more preferably 0.5 cm to 5 cm, for example 2 cm, and has a diameter of preferably 0.1 cm to 1 cm, more preferably 0.25 cm to 0.75 cm, for example 0.5 cm. Along the longitudinal axis L of the vaporiser insert 100, the main part 83 comprises a hollow-cylindrical portion and a portion that does not necessarily taper and has a diameter or cross section that reduces downstream.

The airflow 34 enters the airflow duct 30 at the end face 12 remote from the mouth end 32 (see FIG. 1), flows through the airflow duct 30, and emerges from the airflow duct 30 at the end face 11 that faces the mouth end 32. In the air duct 130, vaporised fluid 50 is added to the airflow 34 in order to administer an aerosol or an aerosol/vapour mixture to the consumer.

Figure 9:
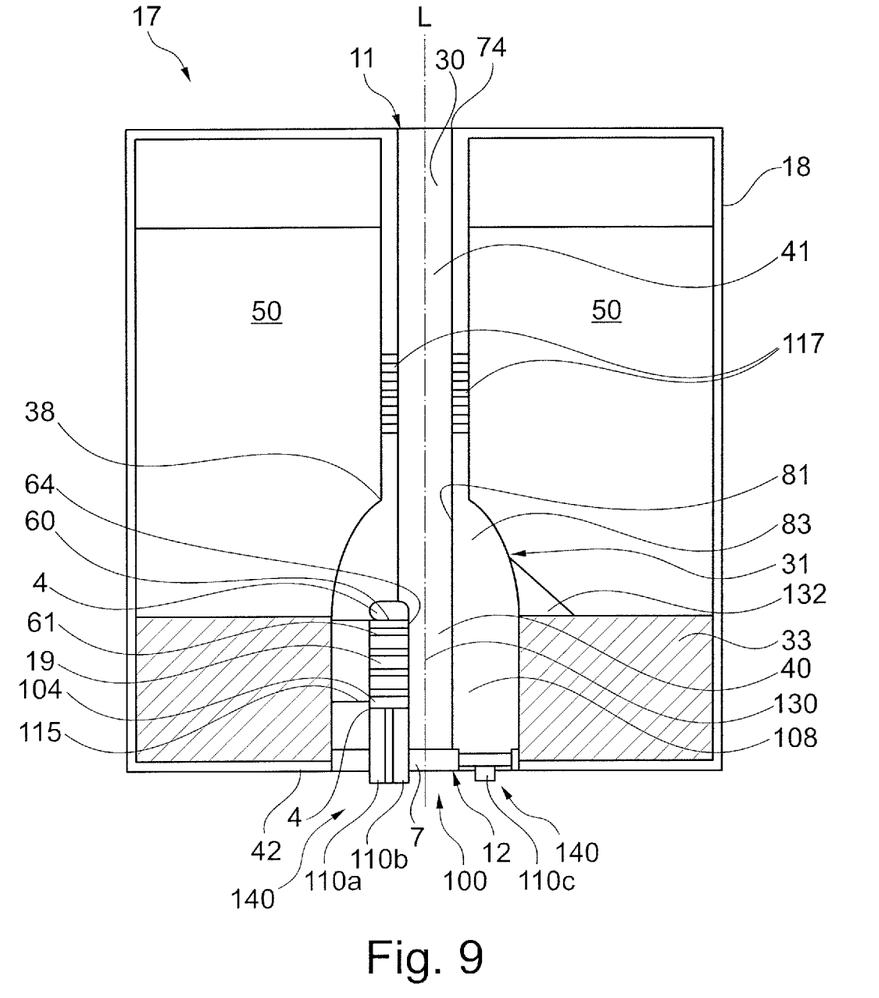
FIG. 9 is a longitudinal section through a vaporiser-tank unit.

The airflow duct 30 comprises a portion that is referred to as the chimney 40 and is assigned to the vaporiser 60, and a vent 41 that is arranged downstream of the vaporiser 60 (see FIG. 9). The vent 41 can be accordingly truncated or shortened by the user and/or manufacturer, depending on the required length.

In this embodiment, the electrical contacting means 140 comprises three electrical contacts 110a, 110b, 110c on a baseplate 7 of the vaporiser insert 100 that is arranged upstream of the vaporiser 60.

The preferably standardised electrical contacting means 140 between the vaporiser insert 1 and for example a base part 16 of the inhaler 10 is used for example for actuating the vaporiser(s) (60) and/or for identifying the cartridge by means of a provided ID chip or another identification method. The electrical contacts 110a, 110b, 110c are preferably defined in a non-rotatable standard arrangement, for example in the form of concentric contact pads for spring bars. A contactless identification method, for example using RFID and/or near field communication (NFC), is conceivable.

The baseplate 7 can be detachably or rigidly connected to the main part 83. The baseplate 7, the chimney 40 and the vent 41 preferably define a standardised unit which is suitable for fluid reservoirs 18 of various shapes. Embodiments without a baseplate 7 are also conceivable. In order that air can flow therethrough, the baseplate 7 advantageously comprises a central opening. Instead of or in addition to the baseplate 7 shown in FIG. 9, the collar 125, visible in FIGS. 2 and 5, can be provided on the main part 83.

FIG. 9 shows the vaporiser-tank unit 17 comprising a fluid reservoir 18 and the vaporiser insert 100 inserted therein. The fluid reservoir 18 comprises a housing having an insertion opening 42 and an outlet opening 74, in which a vaporiser insert 100 can be arranged, in particular pushed or inserted. The vaporiser insert 100 can advantageously be inserted or pushed into the insertion opening 42 along the longitudinal axis L. The fluid reservoir 18 can optionally comprise an installation duct. The optional installation duct can be operatively connected to an insertion opening 42 and an outlet opening 74.

At least one ventilation device 117 can be provided in the airflow duct 30, for example in the vent 41. The ventilation device 117 can comprise a plurality of perforations along the vent 41 for example. In order to prevent liquid escaping through the holes or perforations, the vent 41 or the main part 83 can be created, by means of a suitable material selection, the use of the lotus effect, or structuring of the surface, for example nanostructuring, such that there is as large a contact angle as possible between the surface and the liquid and the surface is fluid-repellent.

The main part 83 can also consist of a semi-permeable material at least in part, which material does not allow any fluid 50 to enter the airflow duct 30 and at the same time allows for ventilation of the fluid reservoir 18.

The vaporiser insert 100 preferably comprises a retaining and/or fastening element 38 for fastening and retaining the vaporiser insert 100 in the insertion opening 42, the outlet opening 74 and/or the installation duct or in the fluid reservoir 18. The retaining and/or fastening element 38 can for example comprise a recess, bulge, lug, groove and/or a latching element. The retaining and/or fastening element 38 can be one-sided and/or non-rotationally symmetric, in order to allow for non-rotatable installation of the vaporiser insert 100 in the fluid reservoir 18. The retaining and/or fastening element 38 retains the vaporiser insert 100 in the fluid reservoir 18 in a stationary manner and prevents displacement and/or twisting of the vaporiser insert 100. As shown in the embodiment, the retaining and/or fastening element 38 can be formed by the shaping of the lateral face 31 of the main part 83. The retaining and/or fastening element 38 shown comprises a tapering of the main part 83 and prevents displacement in the direction of the longitudinal axis L of the vaporiser insert 1.

The retaining and/or fastening element 38 can retain the vaporiser insert 100 in the fluid reservoir 18 in a non-detachable manner, for example by means of adhesive bonding or welding, such that the vaporiser-tank unit 17 is a product in which the vaporiser insert 100 is installed in a fixed manner and such that it cannot be detached by the consumer. Alternatively, use in open tank systems that comprise a fluid reservoir 18 that can be refilled by the user is conceivable.

The retaining and/or fastening element 38 can be designed such that the vaporiser insert 100 can be inserted into and removed from the insertion opening 42, the outlet opening 74 and/or the installation duct, or the fluid reservoir 18. This allows for reversible installation of the vaporiser-tank unit 17 and replacement of the vaporiser insert 100 while keeping the fluid reservoir 18, as a result of which the fluid reservoir 18 and/or the vaporiser insert 100 can be designed as a reusable part. In the embodiments explained, integration of the vaporiser insert 100 into different fluid reservoirs 18 having different tank systems is conceivable.

The basic shape of the cartridge-shaped vaporiser insert 100 is designed such that the vaporiser insert 100 can be installed in various fluid reservoirs 18 in a manner requiring only minimal adjustments and preferably few mechanical interfaces. The vaporiser insert 100 is advantageously connected to the fluid reservoir 18 in a fluid-tight manner in order to prevent a leakage of fluid at the connection point. The connection between the vaporiser insert 100 and the fluid reservoir 18 can be achieved for example by an interference fit, by welding and/or by adhesive bonding, and/or can comprise a seal 120.

Integrating the vaporiser function and the electronic control in the vaporiser insert 100 means that the functional requirements for the fluid reservoir 18 are low and are limited to that of receiving the liquid or the fluid 50. This leaves the shaping of the liquid reservoir 18 or of the housing open, since preferably the only restriction on the housing shape is the recess for the insertion opening 42, the outlet opening 74 and/or the installation duct.

The liquid reservoir 18 can advantageously be filled at least in part or fully by means of a fluid buffer element or liquid supply element 33. The fluid opening 115 is associated with the liquid supply element 33 that is arranged in the fluid reservoir 18. The liquid supply element 33 is advantageously arranged so as to be in contact with the wick structure 19. The liquid supply element 33 is designed to store fluid 50 from the fluid reservoir 18 and to transport said fluid to the wick structure 19. This allows for reliable supply of the wick structure 19 with fluid 50 from the fluid reservoir 18 independently of the filling level, position and/or orientation. Just like the wick structure 19, the liquid supply element 33 can consist of one of the described porous and/or capillary fluid-conducting materials.

A bolt 32 is provided on the lateral face 31 of the main part 83, which bolt can be provided for retaining the liquid supply element 33 within a fluid reservoir 18.

The bolt 32 can function as the retaining and/or fastening element 38 and can assist in displacement-resistant and/or non-rotatable installation of the vaporiser insert 100 in the fluid reservoir 18. The bolt 32 can also be formed around the entire periphery, as a lip on the lateral face 31 of the main part 83. The bolt 32 or the lip is advantageously narrower than the portion of the main part having the largest periphery or than the collar 125, in order to allow for installation of the vaporiser insert 100 by means of being pushed into the liquid reservoir 18.

In the embodiments shown, the main part 83 is designed as a tank inner part for insertion for example into an insertion opening 42 of a fluid reservoir 18. The air duct 130 is formed by the support 4 at least in part. The air duct 130 can be formed by the wall 81 and the support 4 (see FIGS. 2 and 3) and/or by the support 4, for example by two shells 108a, 108b (see FIGS. 4 and 5). It is also conceivable, however, for the air duct 30 to extend through the interior of a support 4, for example a single-shell support 4. For this purpose, the support 4 can be produced, in accordance with the design of the air duct 30, from a plastics material by means of injection moulding, and/or the air duct 130 can be formed in the support 4 for example by drilling or etching following production of the support 4.

EMBODIMENTS

Embodiment 1

Vaporiser insert (100) for an inhaler, in particular an electronic cigarette product (10), comprising:
- at least one electrical vaporiser (60) for vaporising fluid (50) supplied to the vaporiser (60) and for supplying the vaporised fluid to an airflow (34),
- a main part (83) having a lateral face (31) which surrounds an airflow duct (30) through which the airflow (34) can flow,
- at least one fluid opening (115) for supplying vaporisable fluid (50) from the outside into the vaporiser insert (100) and to the vaporiser (60) being arranged on the lateral face (31) of the main part (83),
characterised in that
the vaporiser insert (100) comprises a support (4) for retaining the vaporiser (60),
the support (4) comprising a passage opening (104) that corresponds to the fluid opening (115) in order to supply fluid to the vaporiser (60).

Embodiment 2

Vaporiser insert (100) according to embodiment 1, characterised in that
the support (4) forms an air duct (130) for guiding the airflow (34).

Embodiment 3

Vaporiser insert (100) according to embodiment 2, characterised in that
the air duct (130) is formed between the support (4) and the wall (81) of the vaporiser insert (100), and/or inside the support (4).

Embodiment 4

Vaporiser insert (100) according to any of the preceding embodiments, characterised in that
the support (4) comprises or bears electrical contacting means (140) for electrically contacting the vaporiser insert (100), and/or an electrical lead (105) for the vaporiser (60).

Embodiment 5

Vaporiser insert (100) according to any of the preceding embodiments, characterised in that
electrical contacts (110a, 110b, 110c) are provided on an end face (11, 12) of the vaporiser insert (100).

Embodiment 6

Vaporiser insert (100) according to any of the preceding embodiments, characterised in that
the support (4) bears against a wall (81) of the main part (83).

Embodiment 7

Vaporiser insert (100) according to embodiment 6, characterised in that
the lateral face (31) forms the wall (81) at least in part.

Embodiment 8

Vaporiser insert (100) according to any of the preceding embodiments, characterised in that
the support (4) forms an auxiliary air duct (101) that is different from the air duct (130) and is intended for guiding an auxiliary airflow (102).

Embodiment 9

Vaporiser insert (100) according to any of the preceding embodiments, characterised in that
the support (4) for retaining the vaporiser (60) comprises a ceramic substrate (103).

Embodiment 10

Vaporiser insert (100) according to any of the preceding embodiments, characterised in that
the support (4) is formed of at least one or two shells (108, 108a, 108b), preferably made of plastics material.

Embodiment 11

Vaporiser insert (100) according to any of the preceding embodiments, characterised in that a wick structure (19) that extends through the passage opening (104) is provided.

Embodiment 12

Vaporiser insert (100) according to any of the preceding embodiments, characterised in that
the vaporiser insert (100) has a longitudinal axis (L), and an outlet side (64) of the vaporiser (60) is oriented so as to be in parallel with the longitudinal axis (L).

Embodiment 13

Vaporiser insert (100) according to any of the preceding embodiments, characterised in that
the support (4) comprises a heat conduction element and/or a thermal insulation element.

Embodiment 14

Vaporiser insert (100) according to any of the preceding embodiments, characterised in that
the support (4) comprises a flow, temperature and/or filling level sensor.

Embodiment 15

Vaporiser insert (100) according to any of the preceding embodiments, characterised in that
the support (4) comprises an electronic controller (15).

Embodiment 16

Vaporiser insert (100) according to any of the preceding embodiments, characterised in that the main part (83) is cartridge-shaped or sleeve-shaped.

Embodiment 17

Vaporiser insert (100) according to any of the preceding embodiments, characterised in that
the vaporiser insert (100) can be arranged in, in particular inserted into or pushed into, an external part, in particular a fluid reservoir (18).

Embodiment 18

Vaporiser-tank unit (17) for an electronic cigarette product (10), comprising
a vaporiser insert (100) according to any of the preceding embodiments, and
a fluid reservoir (18), wherein
the vaporiser insert (100) is inserted into the fluid reservoir (18).

Embodiment 19

Electronic cigarette product (10), comprising
a vaporiser-tank unit (17) according to embodiment 18, and
a base part (16) for supplying the vaporiser-tank unit (17) with electrical energy.

The invention claimed is:
1. A vaporiser insert for an inhaler, comprising:
at least one electrical vaporiser for vaporising fluid supplied to the at least one electrical vaporiser and for supplying vaporised fluid to an airflow;
a main part having a lateral face that surrounds an airflow duct through which the airflow can flow;
at least one fluid opening for supplying fluid from outside the vaporiser insert into the vaporiser insert and to the at least one electrical vaporiser being arranged on the lateral face of the main part; and
a support for retaining the at least one electrical vaporiser,
wherein the support comprises a passage opening that corresponds to the at least one fluid opening in order to supply fluid to the at least one electrical vaporiser
wherein the support comprises a substantially plate-shaped main plate,
wherein the passage opening and the at least one fluid opening are configured to connect a fluid reservoir to the at least one electrical vaporiser in a fluid conducting manner so as to supply fluid to be vaporized to the at least one electrical vaporiser, and
wherein the at least one electrical vaporiser is a block consisting of doped silicon.
2. The vaporiser insert according to claim 1,
wherein the support forms an air duct for guiding the airflow.
3. The vaporiser insert according to claim 2,
wherein the air duct is formed between the support and the wall of the vaporiser insert, and/or inside the support.
4. The vaporiser insert according to claim 2,
wherein the support forms an auxiliary air duct for guiding an auxiliary airflow, and wherein the auxiliary air duct is different from the air duct.
5. The vaporiser insert according to claim 1,
wherein the support comprises or bears electrical contacts for electrically contacting the vaporiser insert, and/or an electrical lead for a vaporiser.
6. The vaporiser insert according to claim 1,
wherein the electrical contacts are provided on an end face of the vaporiser insert.
7. The vaporiser insert according to claim 1,
wherein the support bears against a wall of the main part.
8. The vaporiser insert according to claim 7,
wherein the lateral face forms the wall of the main part at least in part.
9. The vaporiser insert according to claim 1,
wherein the support for retaining the at least one electrical vaporiser comprises a ceramic substrate.
10. The vaporiser insert according to claim 9, wherein the ceramic substrate for retaining the at least one electrical vaporiser is arranged around the passage opening, wherein the ceramic substrate thermally decouples the at least one electrical vaporiser and the substantially plate-shaped main plate.
11. The vaporiser insert according to claim 1,
wherein the support is formed of at least one shell.
12. The vaporiser insert according to claim 1, further comprising:
a fluid-conducting wick structure that extends through the at least one fluid opening and extends through the passage opening.
13. The vaporiser insert according to claim 1,
wherein the vaporiser insert has a longitudinal axis (L), and an outlet side of the at least one electrical vaporiser is oriented so as to be in parallel with the longitudinal axis (L).
14. The vaporiser insert according to claim 1,
wherein the support comprises a heat conduction element and/or a thermal insulation element.
15. The vaporiser insert according to claim 1, wherein the support comprises a flow sensor, a temperature sensor, and/or a filling level sensor.

16. The vaporiser insert according to claim 1,
wherein the support comprises an electronic controller.

17. The vaporiser insert according to claim 1,
wherein the main part is cartridge-shaped or sleeve-shaped.

18. The vaporiser insert according to claim 1,
wherein the vaporiser insert is configured to be inserted into or pushed into a fluid reservoir.

19. A vaporiser-tank unit for an electronic cigarette product, comprising:
a vaporiser insert according to claim 1, and
a fluid reservoir,
wherein the vaporiser insert is inserted into the fluid reservoir.

20. An electronic cigarette product, comprising:
a vaporiser-tank unit according to claim 19, and
a base part for supplying the vaporiser-tank unit with electrical energy.

21. An electronic cigarette product, comprising:
a vaporiser insert according to claim 1.

* * * * *